United States Patent
Dacey et al.

(10) Patent No.: US 8,770,405 B2
(45) Date of Patent: *Jul. 8, 2014

(54) DISPENSING PACKAGES FOR MEDICAL DEVICES HAVING TWO COMPONENTS THAT ARE MECHANICALLY INTERLOCKED AND METHODS THEREFOR

(75) Inventors: Denise Marie Dacey, Glen Gardner, NJ (US); Jonathan William Gillespie, Chatham, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/464,434

(22) Filed: May 4, 2012

(65) Prior Publication Data
US 2012/0217176 A1 Aug. 30, 2012

Related U.S. Application Data

(63) Continuation of application No. 12/820,344, filed on Jun. 22, 2010, now Pat. No. 8,517,174.

(51) Int. Cl.
  *A61B 19/02* (2006.01)
(52) U.S. Cl.
  USPC .......................... 206/438; 206/63.3
(58) Field of Classification Search
  USPC .............. 206/438, 784, 363, 738, 756, 524.1, 206/524.3, 524.6, 525.1, 819, 63.3, 400, 206/441; 220/651–654; 229/87.05, 82, 84, 229/72, 76, 125.125
  See application file for complete search history.

(56) References Cited

U.S. PATENT DOCUMENTS

| | | | |
|---|---|---|---|
| 232,273 A | 9/1880 | Jaeger | |
| D29,079 S | 7/1898 | Plunkett | |
| 3,162,307 A | 12/1963 | Regan, Jr. | |
| 4,321,781 A | 3/1982 | Hall | |
| 4,511,035 A * | 4/1985 | Alpern | 206/363 |
| 5,386,912 A | 2/1995 | Holzwarth et al. | |
| 5,487,469 A * | 1/1996 | Roshdy et al. | 206/363 |
| 5,566,821 A | 10/1996 | Brown et al. | |
| 5,584,164 A | 12/1996 | Sinn | |
| 5,699,909 A | 12/1997 | Foster | |
| 5,746,311 A | 5/1998 | Brown et al. | |
| 5,788,063 A | 8/1998 | Van Ness | |

(Continued)

FOREIGN PATENT DOCUMENTS

| | | |
|---|---|---|
| EP | 1346693 | 9/2003 |
| WO | 2004071308 | 8/2004 |

OTHER PUBLICATIONS

International Search Report issued in International Application No. PCT/US2011/041207, mailed Oct. 7, 2011, 4pp.

*Primary Examiner* — Andrew Perreault
(74) *Attorney, Agent, or Firm* — Doherty IP Law Group LLC

(57) ABSTRACT

A package for a flat medical implant includes a flexible outer component, such as Tyvek®, including a first panel and a second panel foldable over said first panel for closing the package, and an inner component, such as paper, mechanically interlocked with the flexible outer component. A flat medical implant is held by the inner component. While the outer and inner components remains mechanically interconnected to one another, the upper ends of the first and second panels of the outer component are peelable away from one another for opening the package and accessing the flat medical implant at an upper end of the package.

24 Claims, 15 Drawing Sheets

(56) References Cited

U.S. PATENT DOCUMENTS

| | | |
|---|---|---|
| 6,032,795 A | 3/2000 | Ehrlund et al. |
| 6,059,112 A * | 5/2000 | Dykstra et al. ................ 206/438 |
| 6,533,112 B2 | 3/2003 | Warnecke |
| 6,752,272 B2 * | 6/2004 | Jones et al. .................. 206/534 |
| 7,090,079 B2 * | 8/2006 | Ehrlund ....................... 206/531 |
| 7,600,634 B2 | 10/2009 | Malinowski et al. |
| 8,517,174 B2 | 8/2013 | Dacey et al. |
| 2005/0113849 A1 * | 5/2005 | Popadiuk et al. ............ 606/151 |
| 2007/0227916 A1 | 10/2007 | Malinowski et al. |
| 2012/0217176 A1 | 8/2012 | Dacey et al. |

* cited by examiner

DISPENSING PACKAGES FOR MEDICAL DEVICES HAVING TWO COMPONENTS THAT ARE MECHANICALLY INTERLOCKED AND METHODS THEREFOR

CROSS REFERENCE TO RELATED APPLICATIONS

The present application is a continuation application of U.S. patent application Ser. No. 12/820,344 filed Jun. 22, 2010, now issued on Aug. 27, 2013 as U.S. Pat. No. 8,517,174, the disclosure of which is hereby incorporated by reference herein.

BACKGROUND OF THE INVENTION

1. Field of the Invention

The present invention generally relates to medical devices, and more specifically relates to packages for medical devices.

2. Description of the Related Art

Medical devices are typically stored in sterile packages prior to being removed from the packages for use during surgical procedures. For example, U.S. Pat. No. 7,600,634 to Malinowski et al. discloses a package for sutures including an envelope, an outer jacket, and an inner retainer that is secured within the outer jacket. The envelope receives the outer jacket and the inner retainer when the outer jacket and the inner retainer are folded. The envelope has a top sheet formed of a clear plastic, such as a polyethylene, and a bottom sheet constructed from paperboard, fiberboard, Tyvek®, aluminum foil or other similar materials. The combination of materials of the top and bottom sheets prevents or impedes the transmission of moisture therethrough. The top sheet and the bottom sheet are generally rectangular in shape, are substantially the same size, and are adhered together along their respective peripheries by an adhesive material.

Commonly assigned U.S. Pat. No. 6,533,112 to Warnecke discloses packaging for surgical sutures having a base with a raised edge and a spiral-like thread duct that opens at a first end thereof to a thread removal zone defined by a recess in the base located adjacent the first end of the thread duct. The base includes a thread tray positioned on an opposite side of the recess from the first end of the thread duct, and a thread holder having a nose extending inwardly from the raised edge of the base above the thread tray. The packaging includes a cover applied to the base above the thread dud. In one embodiment, the cover is made from a piece of cardboard that is coated on its underside with polyethylene. The cardboard cover is suitable for imprinting so that packaging can be easily provided with a product label. In addition, the cardboard cover is adapted to absorb residual quantities of water after a package with surgical suture material has been introduced into an outer wrapper. The cardboard cover also protects the surgical suture material and acts as a lid for the base to reinforce the entire package.

U.S. Pat. No. 5,699,909 to Foster discloses a surgical instrument package including an outer envelope having first and second sheets of microorganism-impervious material that are bonded together around the periphery of each sheet, and a retainer member insertable within the outer envelope for holding a medical product. The retainer member includes a strip of flexible material such as polyethylene terephthalate, polyethylene, vinyl, polypropylene and ethylene vinyl acetate.

In spite of the above advances, there remains a need for a package for medical devices, such as tissue supporting implants, which has enhanced integrity and functionality so that surgical personnel may easily remove and control the medical device as it is removed from the package. There also remains a need for a package for dispensing medical devices that securely locks so that the medical devices do not easily spill out of the packaging when the package is opened. In addition, there is a need for medical packaging which does not require additional adhesive to secure the packaging and the medical products, thereby reducing the bio-burden and the possibility of adhesive leaching into the medical device. There also remains a need for a medical package dispenser whereby a medical device can be inserted into the package during a folding and/or tucking operation, which allows for easy filling of the package without risking folds or bends in the medical device and without risking the medical device catching a surface of the dispenser package during removal of the medical device from the package. There also remains a need for medical packaging that prevents unwanted drops or mishandling, and that allows for easy access and dispensing of the medical product. There also remains a need for medical packaging whereby the product is covered and protected in a sterile environment until immediately prior to use.

Packages for smaller format medical devices are often made entirely of paperboard. Large format packages, however, require an amount of paperboard that is too great for practical use with products requiring a drying cycle. Thus, there is also a need for packaging utilizing a sufficient amount of paperboard that is supplemented with a second material that is less hydrophilic. There also remains a need for packaging that is easy to open so that the medical device stored therein may be easily accessed. Providing a package having this feature is especially challenging where the non-paperboard component is not as structurally supportive as the paperboard component.

SUMMARY OF THE INVENTION

In one embodiment, a package for a medical device preferably includes an outer component, and an inner component mechanically interlocked with the outer component. The inner component is preferably adapted to be disposed inside the outer component when the package is closed. In one embodiment, the package is adapted to be opened while the outer and inner components remain mechanically interlocked together.

In one embodiment, the inner component is desirably stiffer than the outer component. The inner component is preferably more hydrophilic than the outer component. In one embodiment, the outer component is hydrophobic. In one embodiment, the outer component is porous. In one embodiment, the outer component preferably includes a synthetic material, such as Tyvek®, and the inner component includes cellulose material, such as paper or paperboard. Using Tyvek® for the outer component makes the package highly suitable and compatible with ethylene oxide (ETO) sterilization processes.

In one embodiment, one of the outer and inner components desirably includes at least one slit and the other one of the outer and inner components desirably includes at least one tab for mechanically interlocking the outer and inner components together. In one embodiment, the inner component includes a pair of side tabs and the outer component includes slits for receiving the side tabs of the inner component.

In one embodiment, the outer component preferably has a first panel, a second panel adapted to fold over the first panel for closing the package, a first locking slit extending along a first side of the second panel, and a second locking slit extending along a second side of the second panel. The outer component desirably includes a first foldable tab projecting from a first side of the first panel, and a second foldable tab projecting from a second side of the first panel, whereby the first and second locking slits on the second panel are desirably aligned with the first and second foldable tabs on the first panel when the second panel is folded over the first panel.

In one embodiment, the inner component preferably has a first locking tab projecting from a first side of the inner component adapted to mechanically interlock with the first foldable tab of the outer component, and a second locking tab projecting from a second side of the inner component adapted to mechanically interlock with the second foldable tab of the outer component. In one embodiment, when the second panel of the outer component is folded over the first panel of the outer component, the first side locking tab is insertable into the first locking slit on the second panel for closing a first side of the package and the second locking tab is insertable into the second locking slit on the second panel for closing a second side of the package. In one embodiment, the first foldable tab preferably includes a slit adapted to receive the first side locking tab and the second foldable tab preferably includes a slit adapted to receive the second side locking tab.

In one embodiment, the locking tabs on the inner component thread through the slits in the foldable tabs of the outer component for interlocking the inner and outer components together. After the locking tabs have been threaded through the slits of the foldable tabs, the interlocked components (i.e. the locking tabs threaded through the slits of the foldable tabs) are preferably folded together, over the respective sides of the package for closing the sides of the package. The locking tabs of the folded, interlocked components may be inserted into locking slits on the outer component for locking the sides of the package.

In one embodiment, each of the first and second locking tabs includes a rounded lower end and an upper end including a locking recess and a gap toothed tab adjacent the locking recess. The locking recess on each of the first and second lateral locking tabs is preferably oriented toward an opening end of the package. In one embodiment, each of the first and second lateral locking tabs define a first length extending from the rounded lower end to the gap toothed tab thereof and each of the slits on the first and second foldable tabs define a second length, whereby the first length is greater than the second length.

In one embodiment, the first panel of the outer component desirably has a lower end and an upper end with a first upper end locking tab, and the second panel of the outer component desirably has a lower end and an upper end with a second upper end locking tab. In one embodiment, the lower ends of the first and second panels are preferably connected together along a score line that enables the second panel to be folded over the first panel whereupon the upper ends of the first and second panels are in substantial alignment with one another. In one embodiment, when the second panel is folded over the first panel, the first upper end locking tab of the first panel is desirably engageable with the upper end of the second panel and the second upper end locking tab of the second panel is desirably engageable with the upper end of the first panel for closing an upper end of the package.

In one embodiment, the first upper end locking tab preferably includes a first flexible flap adapted to engage the upper end of the second panel and the second upper end locking tab preferably includes a second flexible flap adapted to engage the upper end of the first panel for holding the upper end of the package closed.

In one embodiment, the first side locking tab desirably has a first side with a rounded surface for facilitating insertion of the first side locking tab into the first locking slit on the second panel and a second side with a locking recess adapted to retain the first side locking tab in the first locking slit on the second panel after being inserted into the first locking slit. The second side locking tab may have a first side with a rounded surface for facilitating insertion of the second side locking tab into the second locking slit on the second panel and a second side with a locking recess adapted to retain the second side locking tab in the second locking slit on the second panel after being inserted into the second locking slit.

In one embodiment, the inner component preferably includes a main panel having an upper end and a lower and at least one set of opposing securing elements adapted to releasably secure a medical device to the inner component. In one embodiment, the opposing securing elements are oriented toward the upper end of the main panel for urging release of the medical device from the upper end of the main panel.

In one embodiment, the inner component desirably includes a flexible cover hingedly secured to the lower end of the main panel that is adapted to fold over the main panel for at least partially covering a major face of the inner component. The flexible cover may cover an implant held by the inner component.

In one embodiment, at least one of the first and second panels of the outer component preferably includes a window for providing visual access inside the package when the package is closed.

In one embodiment, a package for a flat medical implant preferably includes a flexible outer component including a first panel and a second panel foldable over the first panel for closing the package, an inner component mechanically interlocked with the flexible outer component, and a flat medical implant held by the inner component. The upper ends of the first and second panels are desirably peelable away from one another while the outer and inner components remains mechanically interconnected together for opening the package and accessing the flat medical implant at an upper end of the package.

In one embodiment, the flat medical implant preferably includes a laminate having a surgical mesh and at least one absorbable layer overlying the surgical mesh. The inner component is desirably adapted to remove moisture present in the medical implant and inside the package.

In one embodiment, the medical device or flat medical implant preferably has a length of about 5-60 cm and a width of about 10-30 cm. The flat implant may have an oval, circular, square or rectangular shape. In one embodiment, the weight ratio of the inner component to the at least one absorbable layer of the flat medical implant is between about 3.9:1-5.5:1. In one embodiment, the weight of the absorbable part of a small implant is about 1.17 grams and the weight of the inner component of the package is about 5.4 grams for a weight ratio of about 4.6:1. In one embodiment, the weight of the absorbable part of a medium implant is about 2.34 grams and the weight of the inner component of the package is about 12.8 grams for a weight ratio of about 5.5:1: In one embodiment, the weight of the absorbable part of a large implant is about 4.1 grams and the weight of the inner component of the package is about 20.7 grams for a weight ratio of about 5.1:1. In one embodiment, the weight of the absorbable part of an extra large implant is about 5.86 grams and the weight of the inner component of the package is about 23.1 grams for a weight ratio of about 3.9:1.

In one embodiment, a bi-component dispensing package for medical devices desirably includes an inner component having a first stiffness and at least two locking tabs. The two locking tabs preferably have a locking recess on one side and a rounded edge on an opposing side. The bi-component dispensing package preferably includes an outer component having a second stiffness that is less than the first stiffness. The outer component preferably has locking slots, whereby the locking tabs of the inner component are mechanically interlocked with the slots of the outer component with a locking recess on the locking tabs being in close proximity to an opening in the folder. In one embodiment, one component of the bi-component dispensing folder is flexible with respect to the other component and has lower relative hydrophilicity relative to the other component. In one embodiment, the inner component may be a cellulose material such as paperboard and the outer component may be a synthetic material such as Tyvek®.

In one embodiment, locking tabs on the sides of the inner component preferably lock with slots in the outer component (i.e., a Tyvek® folder) to form an integrated dispensing package or folder. The paper inner component in combination with the Tyvek® outer component work together to provide a secure package locking mechanism. In one embodiment, the paper insert is preferably placed on the inside of the folder and desirably has tabs that extend via slits or slots in the Tyvek® folder outside of the Tyvek® folder. The Tyvek® folder also has side tab extensions. These tabbed features are then wrapped around the paper insert as the paper insert is folded along designated score lines. The folder is finished and locked by having the paper tabs lock into place within locking slits on a panel of the Tyvek® folder.

In one embodiment, the package is easily opened for dispensing the medical device by unlocking two upper end locking tabs and folding or peeling away the two upper ends of the Tyvek® folder. After the two upper ends of the Tyvek® folder have been peeled away, the medical device, supported by the inner paper component, preferably projects from the upper end of the package for dispensing the flat medical device in the sterile field. The Tyvek® component of the dispenser package provides breathability, and the paper component desirably provides rigidity and serves a desiccant to remove excess moisture from the environment within the package. In one embodiment, the side of the paper touching the medical device is preferably coated or calendared to ensure slippage of the medical device during removal of the medical device from the dispensing folder. The folder design may be scaled to size to accommodate medical devices having various sizes.

These and other preferred embodiments of the present invention will be described in more detail below.

BRIEF DESCRIPTION OF THE DRAWING

FIG. 4A-1 shows a locking tab of the inner component passing through a slot in a folding tab of the outer component, in accordance with one embodiment of the present invention.

FIG. 4F-1 shows a side view of the locking tab shown in FIG. 4F.

DETAILED DESCRIPTION

Figure 1:
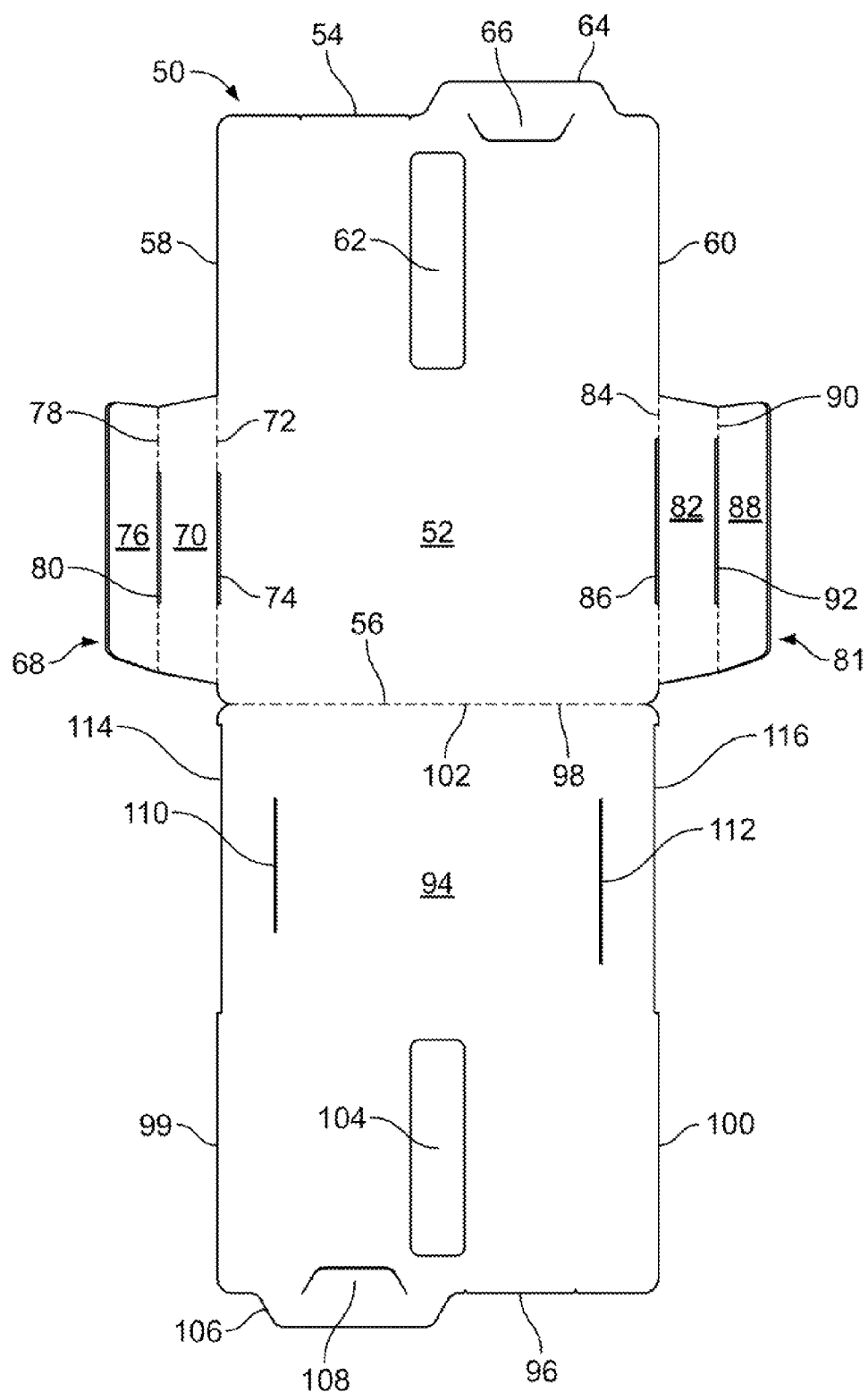
FIG. 1 shows a top view of an outer component of a package for a medical device, in accordance with one embodiment of the present invention.

Referring to FIG. 1, in one embodiment, a package for medical devices, such as flat tissue supporting implants, preferably includes a first or outer component 50 having a first panel 52 with an upper edge 54, a lower edge 56, a first lateral edge 58 and a second lateral edge 60. The first panel 52 preferably includes a first window 62 that is adapted to enable medical personnel to visually confirm whether a medical device is disposed within the package. The first panel 52 preferably includes a first upper locking tab 64 having a first flexible flap 66, which is desirably located adjacent the upper edge 54 of the first panel 52. The first panel 52 desirably includes a pair of foldable side tabs that may be used for both coupling the outer component 50 with an inner component and for closing the sides of the package, as will be described in more detail herein.

In one embodiment, the pair of foldable side tabs preferably includes a first foldable side tab 68 that is integrally formed with the first lateral edge 58 of the first panel 52. The first foldable side tab 68 preferably includes a first foldable part 70 that is secured to the first lateral edge 58 of the first panel 52 along a first score line 72. In one embodiment, a first elongated slot 74 preferably extends between the first lateral edge 58 of the first panel 52 and the first foldable part 70. The first foldable side tab 68 desirably includes a second foldable part 76 that is adapted to fold relative to the first foldable part 70. The second foldable part 76 is desirably connected with the first foldable part 70 along a second score line 78. A second elongated slot 80 desirably extends between the second foldable part 76 and the first foldable part 70.

In one embodiment, the outer component 50 of the package desirably includes a second foldable side tab 81 secured to the second lateral edge 60 of the first panel 52. The second foldable side tab 81 desirably includes a first foldable part 82 that is secured to the second lateral edge 60 along a first score line 84. A first elongated slot 86 desirably extends between the first foldable part 82 and the second lateral edge 60 of the first panel 52. The second foldable tab 81 desirably includes a second foldable part 88 that is secured to the first foldable part 82 via a second score line 90. A second elongated slot 92 preferably extends between the second foldable element 88 and the first foldable element 82 of the second foldable tab 81.

In one embodiment, the outer component 50 of the package preferably includes a second panel 94 that is connected with the first panel 52. The second panel 94 desirably includes an upper edge 96, a lower edge 98 connected to the lower edge 56 of the first panel 52, a first lateral edge 99 and a second lateral edge 100. The lower edge 56 of the first panel 52 and the lower edge 98 of the second panel 94 are desirably connected together along a score line 102, which enables the second panel 94 to be folded over the first panel 52 for closing the package around a medical device disposable between the panels 52, 94.

In one embodiment, the second panel 94 desirably includes a second window 104 that enables medical personnel to determine whether a medical device (e.g. a tissue supporting implant) is located between the first and second panels 52, 94 when the package is closed. The second panel 94 desirably includes a second upper locking tab 106 having a flexible locking flap 108. In one embodiment, when the second panel 94 is folded over the first panel 52 for closing the package, the second locking flap 108 of the second upper locking tab 106 desirably engages the upper edge 54 of the first panel 52, and the first locking flap 66 of the first upper locking tab 64 desirably engages the upper edge 96 of the second panel 94 for holding the upper edges 54, 96 of the respective first and second panels 52, 94 of the outer component 50 together (i.e. in a closed position).

In one embodiment, the second panel 94 of the outer component 50 desirably includes a first locking slot 110 that preferably extends adjacent the first lateral edge 99 of the second panel and a second locking slot 112 that preferably extends adjacent the second lateral edge 100 of the second panel 94. The first and second locking slots 110, 112 are desirably parallel to one another and to the respective first and second lateral edges 99, 100 of the second panel 94.

In one embodiment, the outer component 50 of the package is preferably made of a flexible material. In one embodiment, the outer component 50 is preferably made of a relatively hydrophobic material. In one embodiment, the outer component 50 is made of a synthetic material such as Tyvek®.

In one embodiment, the second panel 94 desirably includes a first cutout 114 that preferably extends between the lower edge 98 of the second panel 94 and part of the way toward the upper edge 96 of the second panel 94. The second panel 94 also preferably includes a second cutout 116 that extends between the lower edge 98 of the second panel 94 and part of the way toward the upper edge 96 thereof. The cutout sections 114, 116 define a slightly narrower section of the second panel 94 that preferably enables more efficient folding and assembly of the package, as will be described in more detail below. The cutout sections 114, 116 also preferably provide for a more compact package when the package is fully assembled.

Figure 2A:
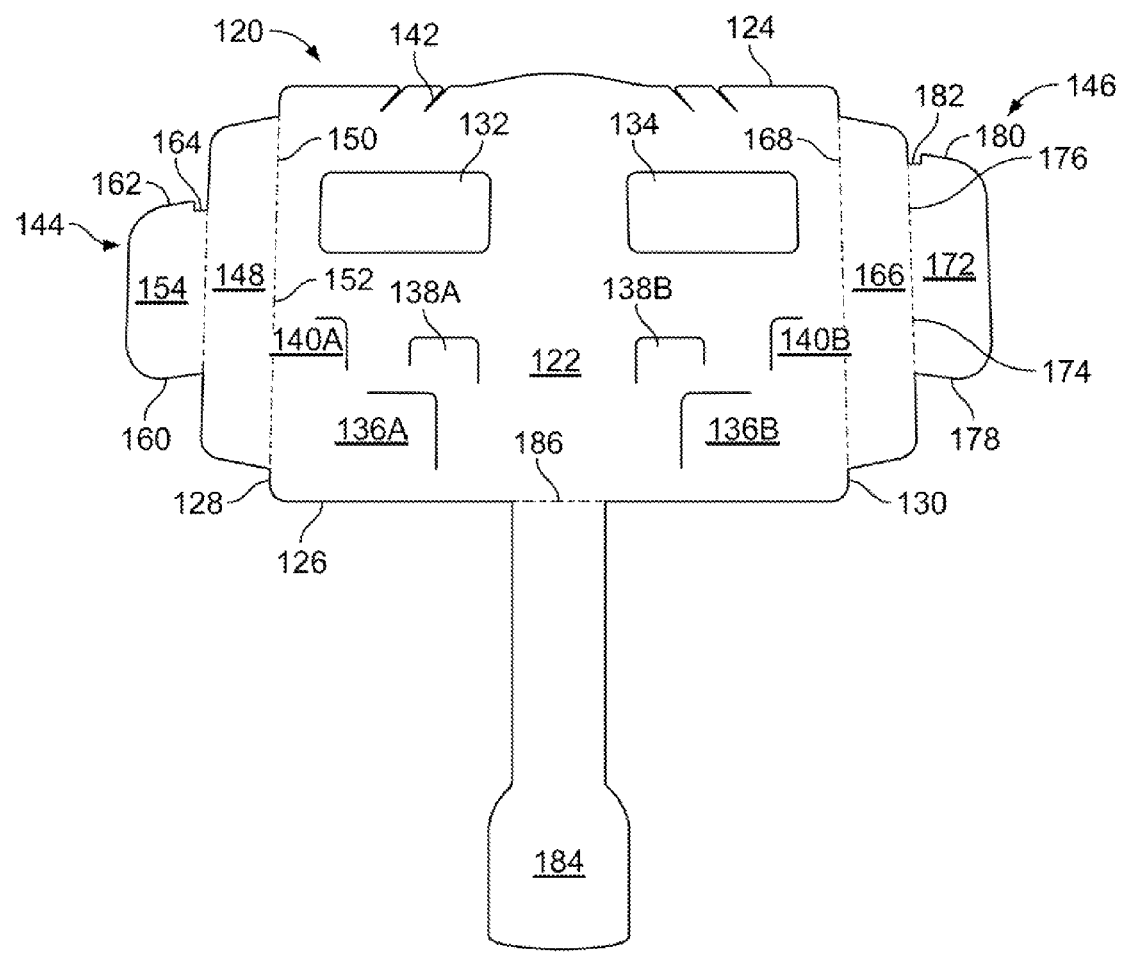
FIG. 2A shows a top view of an inner component of a package for a medical device, in accordance with one embodiment of the present invention.
Figure 2B:
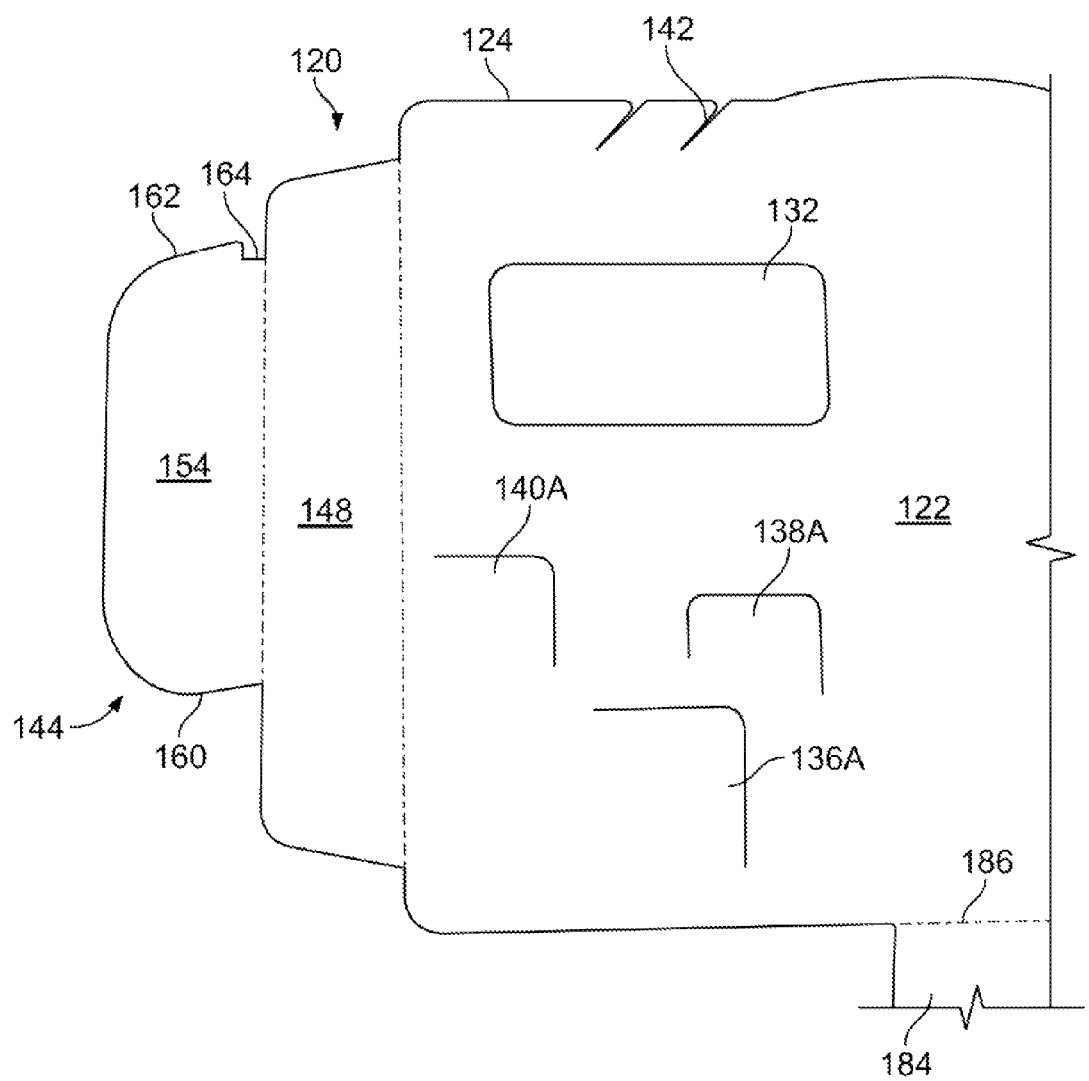
FIG. 2B shows a magnified view of a section of the inner component shown in FIG. 2A.

Referring to FIGS. 2A and 2B, in one embodiment, a package for medical devices preferably includes a second or inner component 120 that is adapted to be assembled with the outer component 50 of FIG. 1. In one embodiment, the inner component 120 is preferably made of a sturdier and more hydrophilic material than the outer component. In one embodiment, the inner component 120 is made of cellulose material such as paper or paperboard. The inner component may act as a desiccant material for removing excess moisture from inside an enclosed package or from a medical device stored in the package.

In one embodiment, the inner component 120 desirably includes a main panel 122 having an upper edge 124, a lower edge 126, a first lateral edge 128 and a second lateral edge 130. The main panel 122 desirably includes a first window 132 and a second window 134. In one embodiment, the first and second windows 132, 134 are formed for minimizing the amount of material that comprises the inner component 120.

In one embodiment, the inner component 120 desirably includes a plurality of flexible flaps and/or slots that may be used for holding a medical implant on the inner component 120. In one embodiment, the inner component 120 desirably includes a first set of flexible flaps 136A, 136B, a second set of opposing flexible flaps 138A, 138B, and a third set of opposing flexible flaps 140A, 140B for accommodating medical devices having a range of sizes. In one embodiment, two or more sets of the flexible flaps may be used for securing a medical implant to the inner component 120. In one embodiment, the upper edge 124 of the main body 122 of the inner component has one or more locking slits 142 that are cut into the upper edge 124 thereof. The one or more locking slits 142 are preferably adapted to accommodate and hold medical devices, such as surgical meshes, to the inner component 120. A plurality of locking slits 142 may be provided on the inner component 120 for accommodating medical implants having different sizes and shapes. In one embodiment, the flexible flaps and/or locking slits face toward the upper edge 124 of the main body 122 so that a medical device may be removed from the package toward the upper end 124 of the main panel 122.

In one embodiment, the flexible flaps and/or locking slits on the inner component 120 function as restraining elements adapted to securely hold the medical device to the inner component until it is time to remove (e.g. by sliding action) the device from the package. In one embodiment, when the package is at least partially opened, the medical device remains securely held to the inner component 120 by the flexible flaps 136, 138, 140 and/or the locking slits 142. The flexible flaps and/or the locking slits are adapted to release the medical device from the inner component 102 for dispensing the medical device from the package. The medical device may be removed by sliding the medical device from the flexible flaps and the locking slits and toward the upper end of the inner component. The restraining features described in this paragraph provide excellent product control in a sterile environment, which greatly reduces or eliminates the likelihood that the medical device will be dropped or damaged upon opening the package. In one embodiment, the restraining elements are adapted to releasably hold the medical device to the inner component without damaging the medical device.

In one embodiment, the inner component 120 preferably includes a first lateral locking tab 144 projecting from the first lateral edge 128 of the main panel 122 and a second lateral locking tab 146 projecting from a second lateral edge 130 of the main panel 122. In one embodiment, the first lateral locking tab 144 desirably includes a first foldable part 148 that is hingedly connected to the first lateral edge 128 of the main panel 122 along a first score line 150. In one embodiment, an elongated slot 152 desirably extends between the first foldable part 148 and the first lateral edge 128 of the main panel 122. The first lateral locking tab 144 desirably includes a second foldable part 154 that is hingedly connected with the first foldable part 148 along a second score line 156. A second elongated slot 158 desirably extends between the first foldable part 148 and the second foldable part 154. In one embodiment, a lower end 160 of the second foldable part 154 has a rounded surface and an upper end 162 of the second foldable part 154 preferably includes a locking recess 164.

In one embodiment, the second lateral locking tab 146 preferably includes a first foldable part 166 that is hingedly connected with the second lateral edge 130 of the main panel 122 along a first score line 168. An elongated slot 170 desirably extends between the first foldable part 166 and the second lateral edge 130 of the main panel 122.

The second lateral locking tab 146 desirably includes a second foldable part 172 that is preferably hingedly connected with the first foldable part 166 along a second score line 174. A second elongated slot 176 desirably extends between the inner edge of the second foldable part 172 and the outer edge of the first foldable part 166. The second foldable part 172 desirably includes a lower end 178 having a rounded surface and an upper end 180 including a locking recess 182. As will be described in more detail below, the rounded surface at the lower end 178 of the second foldable part 172 and the locking recess 182 at the upper end of the second foldable part preferably enable easier assembly and interlocking of the inner component 120 of the package with the outer component 50 (FIG. 1) of the package. The locking recess 182 at the upper end 180 of the second foldable part 172 preferably insures that the outer and inner components 50, 120 of the package remain interlocked together after assembly.

In one embodiment, the locking recesses 164, 182 on the respective first and second lateral locking tabs 144, 146 are preferably oriented toward the upper end 124 of the main panel. When the inner component 120 is assembled and interlocked with the outer component 50 of FIG. 1, the locking recesses are desirably oriented toward the opening end of the package (i.e. toward the upper edge 54 of the first panel 52 of the outer component).

In one embodiment, the inner component 120 of the package desirably includes a foldable cover 184 that is hingedly connected with the lower end 126 of the main panel 122 along a horizontally extending score line 186. In one embodiment, after a medical implant is connected with the inner component 120 via one or more of the flexible flaps 136A, 136B, 138A, 138B, 140A, 140B or locking slits 142, the cover 184 may be folded along the score line 186 over the medical implant and the main panel 122 to insure that the medical implant does shift below the lower edge 126 of the main panel 122. The foldable cover 184 desirably at least partially covers and protects the medical implant when it is secured to the inner component 120 to provide at least some protection for the medical implant.

Figure 3A:
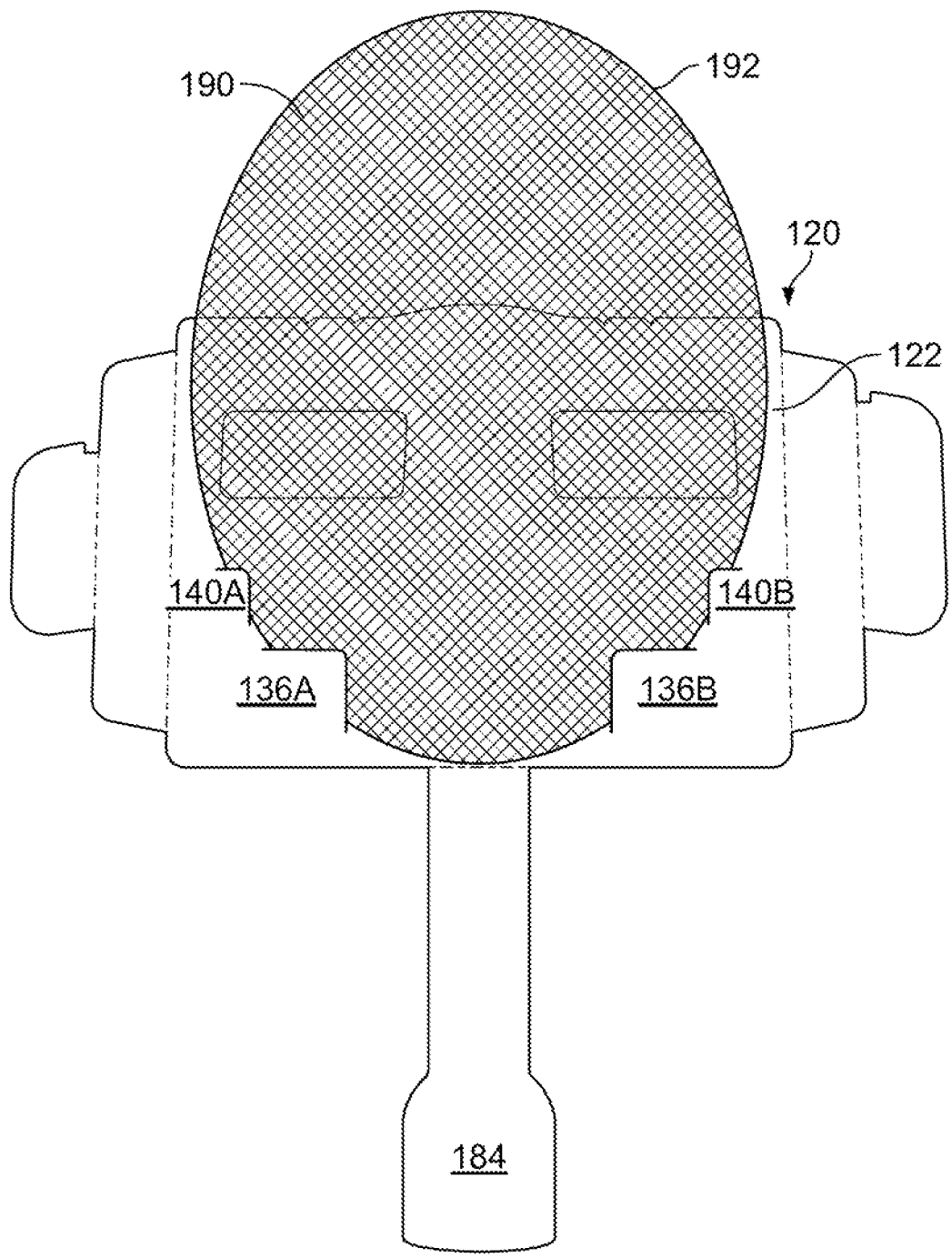
FIG. 3A shows a medical device held by the inner component shown in FIGS. 2A and 2B, in accordance with one embodiment of the present invention.

Referring to FIG. 3A, in one embodiment, a medical implant 190 is secured to the inner component 120 of the package. In the particular embodiment shown in FIG. 3A, the medical implant 190 is a surgical mesh having a peripheral edge 192. The peripheral edge 192 of the implant 190 is preferably inserted under the first set of opposing flexible flaps 136A, 136B and the third set of opposing flexible flaps 140A, 140B to hold the medical implant 190 securely in place atop the main panel 122 of the inner component 120. In one embodiment; the medical implant is a surgical mesh disclosed in commonly assigned U.S. patent application Ser. No. 12/815,275, filed Jun. 14, 2010, and U.S. Design patent application Ser. No. 29/363,759, filed Jun. 14, 2010, the disclosures of which are hereby incorporated by reference herein.

Figure 3B:
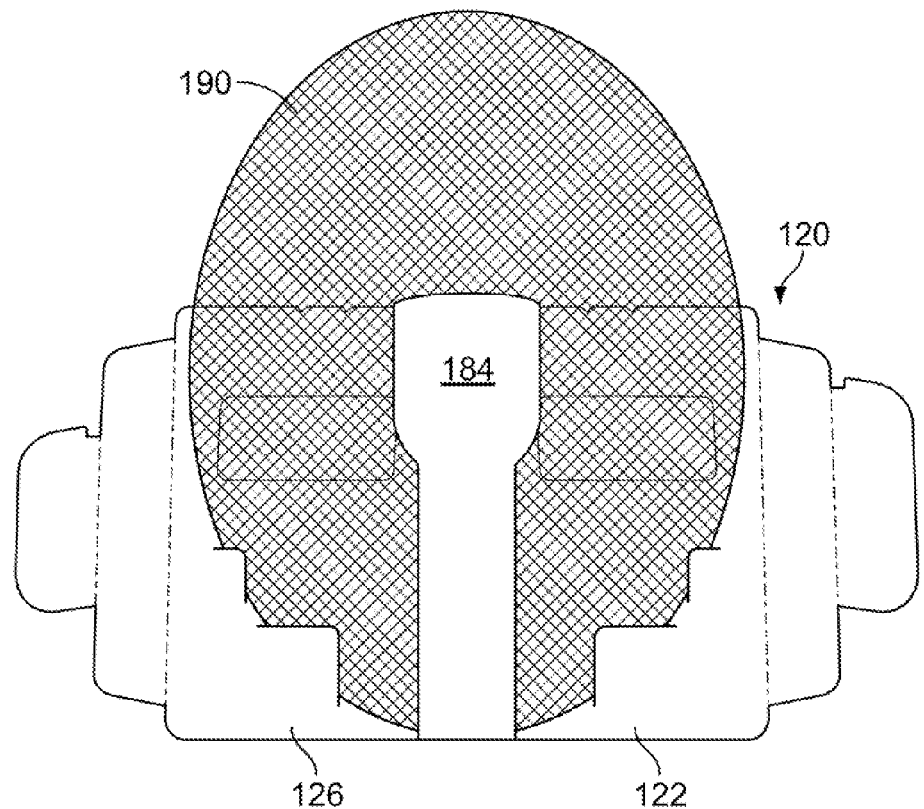
FIG. 3B shows the inner component and the medical device of FIG. 3A with a foldable cover overlying the medical device.

Referring to FIG. 3B, in one embodiment, after the medical implant 190 is secured to the inner component 120, the foldable cover 184 may be folded into the position shown in FIG. 3B for covering at least a portion of the medical implant 190. Although the functions of the foldable cover 184 are not limited by any particular theory of operation, it is believed that the foldable cover 184 at least partially protects the medical implant 190 and prevents the medical implant 190 from shifting below the lower edge 126 of the main body 122 of the inner component 120.

Figure 3C:
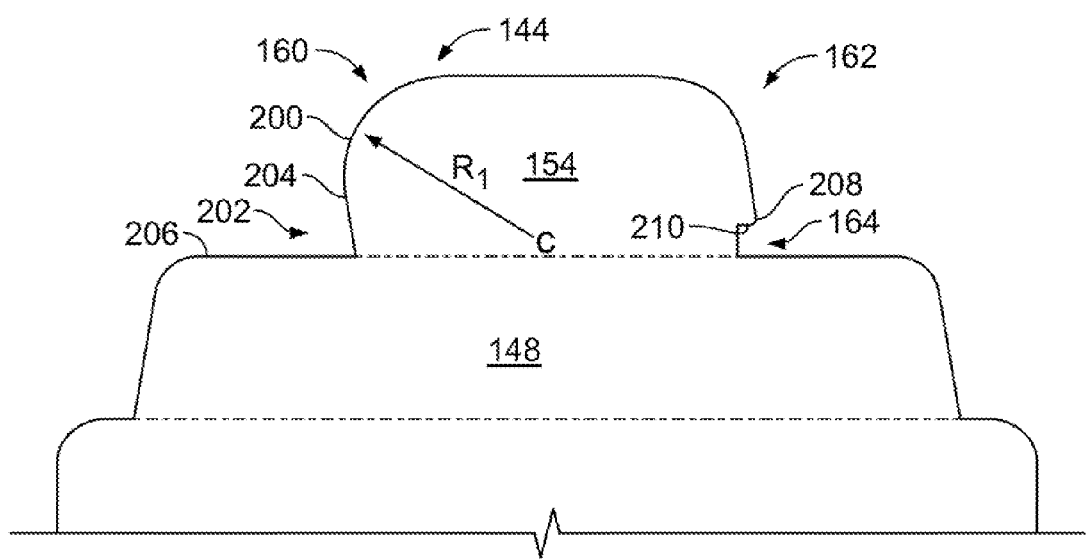
FIG. 3C shows a first lateral locking tab of the inner component of FIG. 2A including a first foldable part and a second foldable part.

Referring to FIG. 3C, in one embodiment, the second foldable part 154 of the first lateral locking tab 144 desirably includes a rounded lower end 160 having a bulbous section 200 defining a radius $R_1$ measured from a center C of the second foldable part. In one embodiment, the radius $R_1$ is approximately 10-15 mm and more preferably about 13 mm. The rounded lower end 160 also preferably includes a recessed section 202 defined by a recessed line 204 that extends inwardly between the bulbous section 200 and an outer edge 206 of the first foldable part 148 of the first lateral locking tab 144. The second foldable part 154 of the first lateral locking tab 144 desirably includes an upper end 162 having a locking recess 164 including a gap toothed tab 208 having a lower edge 210 that is spaced from the outer edge 206 of the first foldable part 148.

Figure 3D:
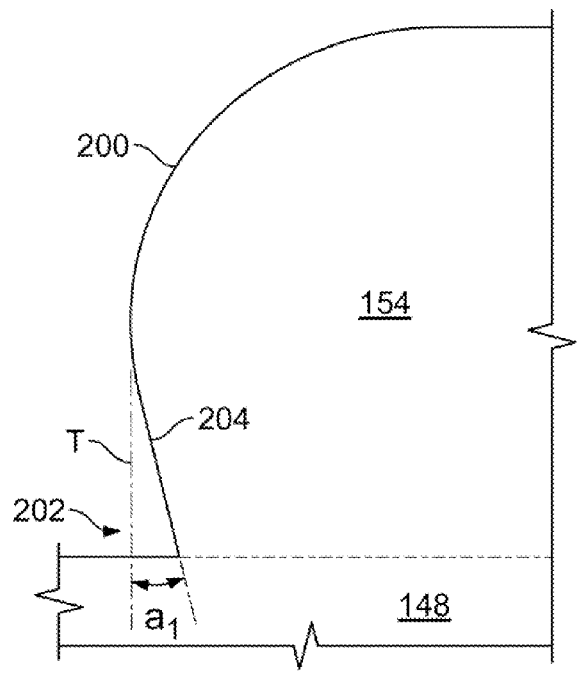
FIG. 3D shows a lower end of second foldable part shown in FIG. 3C.

Referring to FIG. 3D, a tangent line T of the bulbous section 200 and the recessed line 204 define an angle $\alpha_1$ of about 75-80° and more preferably about 78°. When the second foldable part 154 is passed through the slit 80 between the first foldable part 70 and the second foldable part 76 of the first foldable tab 68 (FIG. 1) for interlocking the first and second components together, the recessed section 202 preferably sits against a first end of the slit 80 with the bulbous section 200 extending beyond the first end of the slit 80 for holding the second foldable part 154 in the slit 80.

Figure 3E:
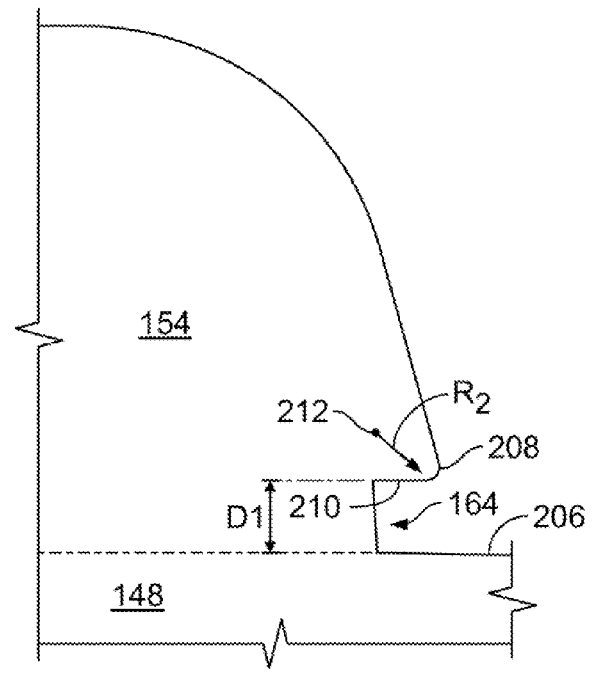
FIG. 3E shows an upper end of the second foldable part shown in FIG. 3C.

Referring to FIG. 3E, in one embodiment, the lower edge 210 of the gap toothed tab 208 is spaced from the outer edge 206 of the first foldable part 148 by a distance $D_1$ of about 3 mm. The gap toothed tab 208 has a radius $R_2$ of about 2 mm from a center point 212. In one embodiment, after the recessed section 202 of the second foldable part 154 is seated against the first end of the slit 80 (FIG. 1), the gap toothed tab 208 is preferably passed through the slit 80 so that the second end of the slit is seated in the locking recess 164 and the gap toothed tab 208 extends beyond the second end of the slit 80.

Figure 4A:
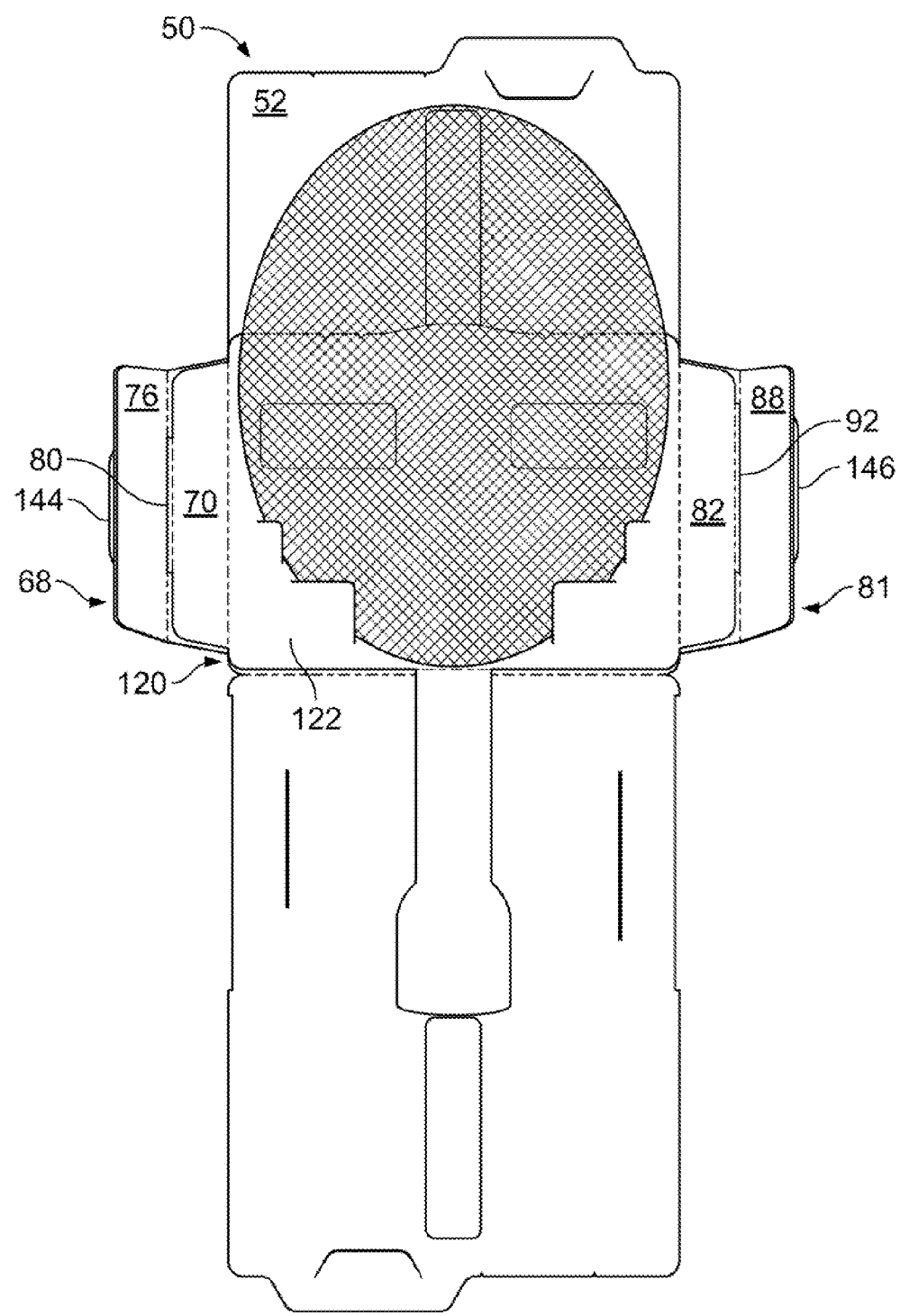
FIGS. 4A-4G show a method of assembling a package for a medical device, in accordance with one embodiment of the present invention.
Figures 1, 4A:
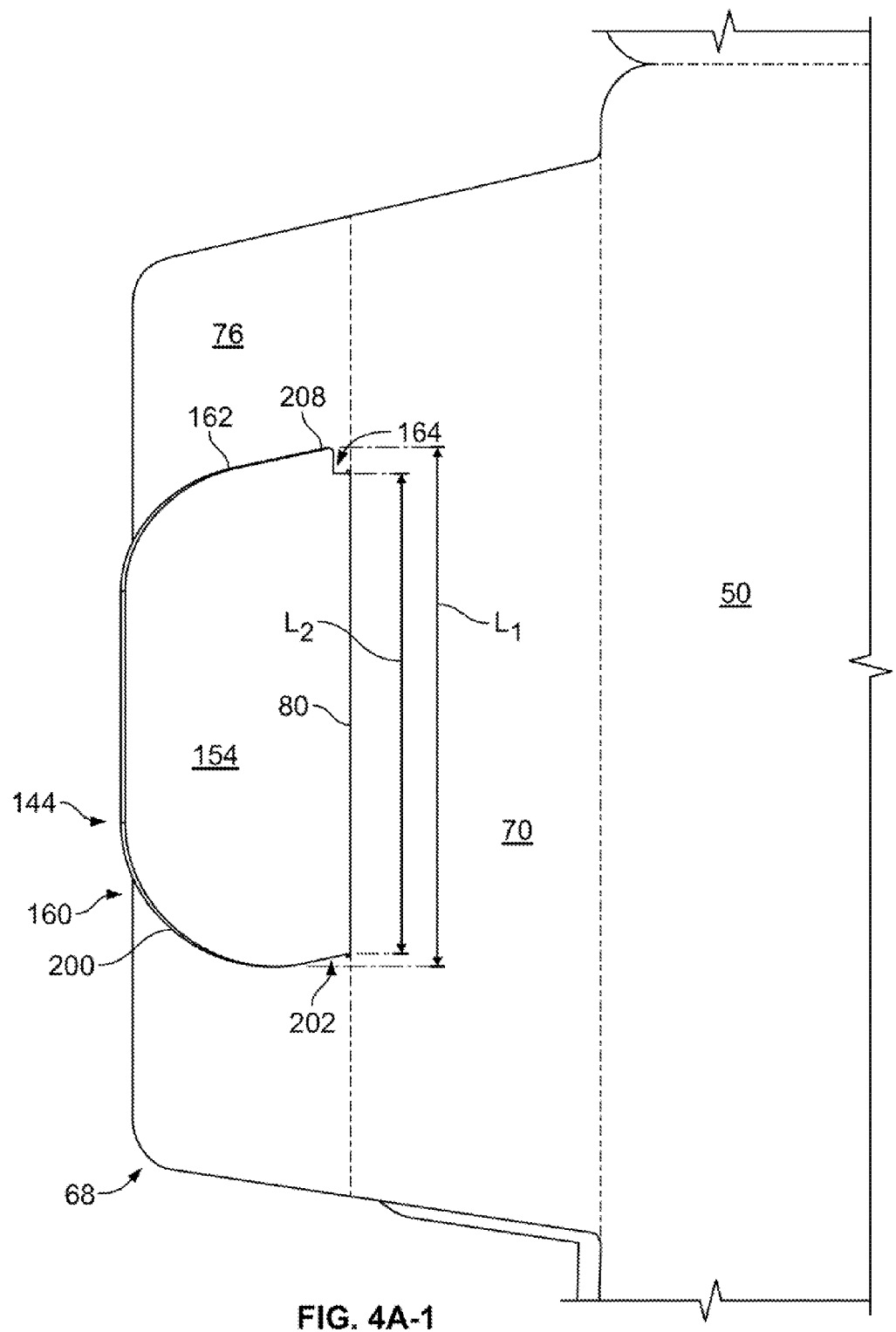

Referring to FIG. 4A, in one embodiment, in order to assemble the outer and inner components together into a package, the inner component 120 is preferably positioned atop the outer component 50 with the main panel 122 of the inner component overlying the first panel 52 of the outer component 50. The first and second locking tabs 144, 146 of the inner component 120 are preferably aligned with the first and second foldable tabs 68, 80 of the outer component 50. In order to securely assembly the inner component 120 with the outer component 50, the first locking tab 144 is desirably passed through the second elongated slit 80 extending between the first foldable part 70 and the second foldable part 76 of the first foldable tab 68. Similarly, the second locking tab 146 is desirably passed through the second slot 92 extending between the first foldable part 82 and the second foldable part 88 of the second foldable tab 80.

FIG. 4A-1 shows a magnified view of the first locking tab 144 of the inner component passing through the elongated slot 80 extending between the first foldable part 70 and the second foldable part 76 of the first foldable tab 68 of the outer component 50. The first locking tab 144 desirably has a first length $L_1$ that is greater than the second length $L_2$ of the elongated slot 80. In one embodiment, $L_1$ is about 0.9-1.3 mm longer than $L_2$, and more preferably about 1.0 mm longer. The rounded lower edge 160 of the second foldable part 154 desirably facilitates passing the first locking tab 144 through the elongated slot 80. The recessed section 202 at the lower end 160 preferably sits against a first end of the slit 80 with the bulbous section 200 preferably extending beyond the first end of the slit 80 for holding the second foldable part 154 in the slit 80.

The locking recess 164 at the upper end 162 of the second foldable part 154 ensures that the first locking tab 144 remains connected to the first foldable tab 68. In one embodiment, after the recessed section 202 of the second foldable part 154 is seated against the first end of the slit 80, the gap toothed tab 208 is preferably passed through the slit 80 so that the second end of the slit is seated in the locking recess 164 and the gap toothed tab 208 extends beyond the second end of the slit 80. The second lateral locking tab (not shown) of the inner component preferably has the same features as described for the first lateral locking tab and is desirably coupled with the second foldable tab 81 of the outer component 50 (FIG. 1) in a similar manner.

Figure 4B:
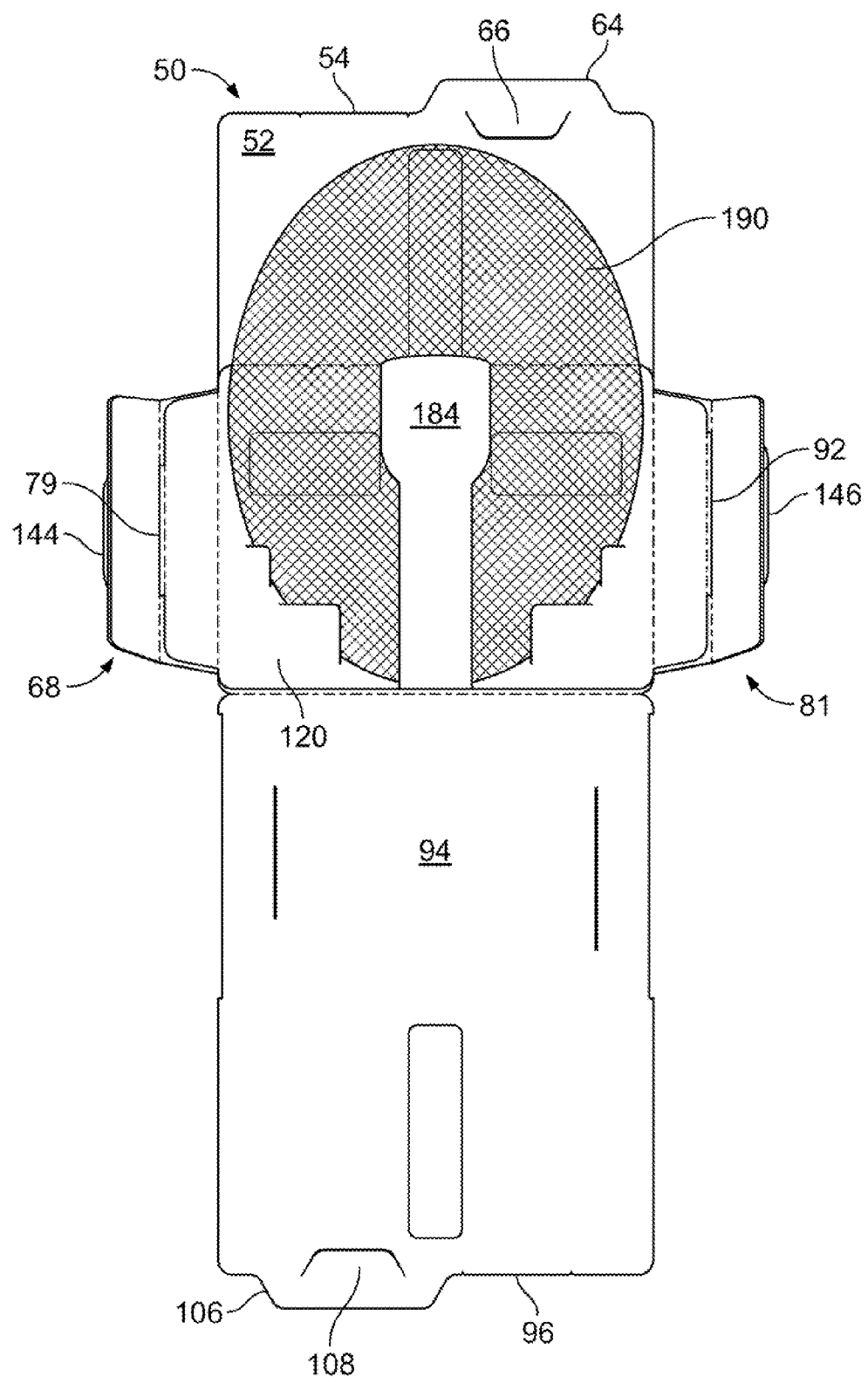

Referring to FIG. 4B, in one embodiment, after the first and second locking tabs 144, 146 have passed through the elongated slits 79, 92 of the respective first and second foldable tabs 68, 80, the foldable cover 184 may be folded toward the upper edge 124 of the main panel 122 of the inner component 120 for at least partially covering the medical implant 190 secured to the inner component 120 and preventing the medical implant 190 from shifting below the lower edge 126 of the inner component.

Figure 4C:
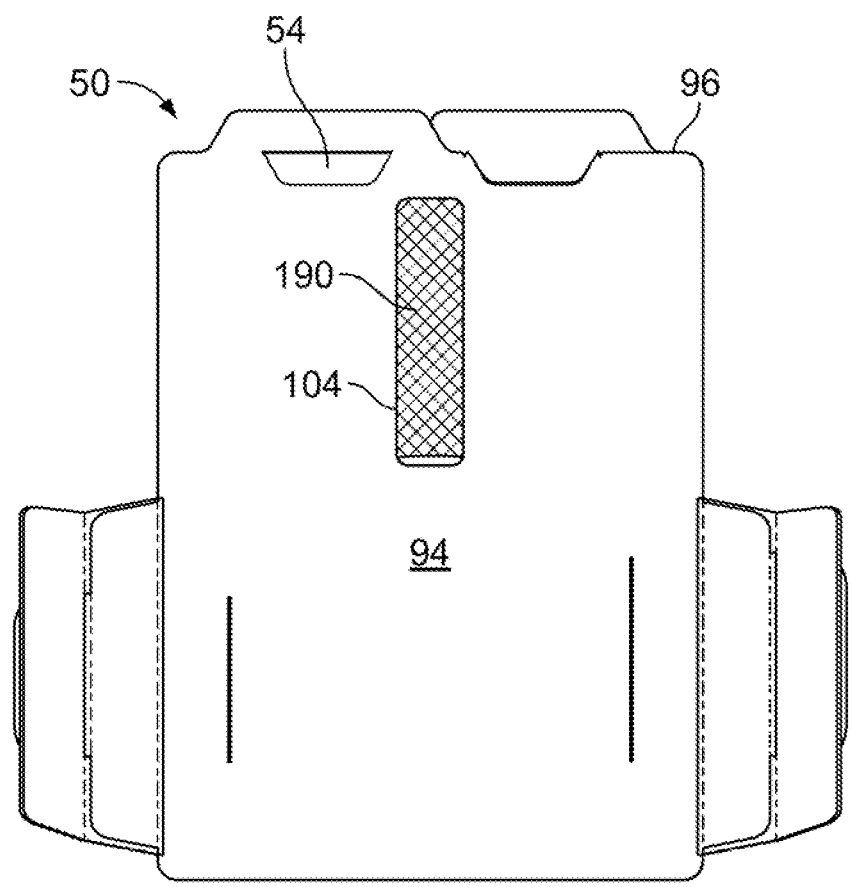

Referring to FIGS. 4B and 4C, in one embodiment, the second panel 94 is folded over the first panel 52 of the outer component 50 so that the upper edge 96 of the second panel 94 is aligned with the upper edge 54 of the first panel 52. The locking flap 108 of the second locking tab 106 preferably engages the upper edge 54 of the first panel 52, and the first locking flap 66 of the first locking tab 64 preferably engages the upper edge 96 of the second panel 94 for holding the upper ends of the panels 52, 94 closed. Referring to FIG. 4C, the medical implant 190 is visible through the second window 104 of the second panel 94.

Figure 4D:
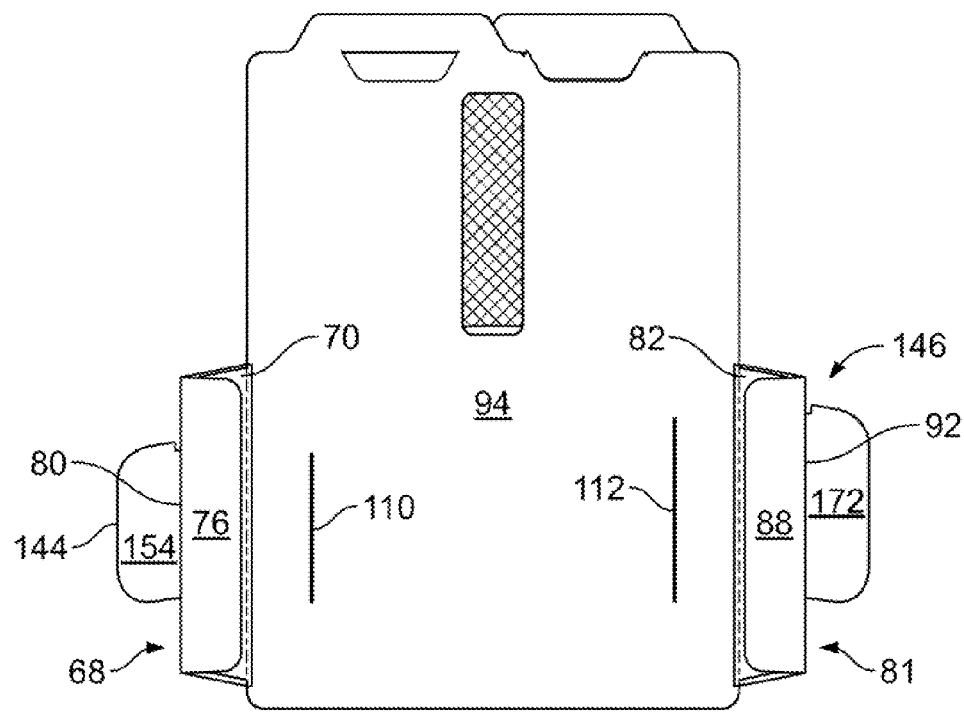

Referring to FIG. 4D, in one embodiment, after the second foldable part 154 of the first lateral locking tab 144 is passed through the elongated slot 79 extending between the first foldable part 70 and the second foldable part 76 of the first foldable tab 68, the second foldable part 76 of the first foldable tab 68 is preferably folded over the first foldable part 70 of the first foldable tab 68. In one embodiment, after the second foldable part 172 of the second lateral locking tab 146 is passed through the elongated slit 92 extending between the first foldable part 82 and the second foldable part 88 of the second foldable tab 80, the second foldable part 88 of the second foldable tab 80 is preferably folded over the first foldable part 82 of the second foldable tab 80. When the second panel 94 is closed over the first panel of the outer component, the second foldable part 154 of the first lateral locking tab 144 is preferably in alignment with the first locking slot 110 of the second panel 94, and the second foldable part 72 of the second lateral locking tab 146 is preferably in alignment with the second locking slot 112 of the second panel 94.

Figure 4E:
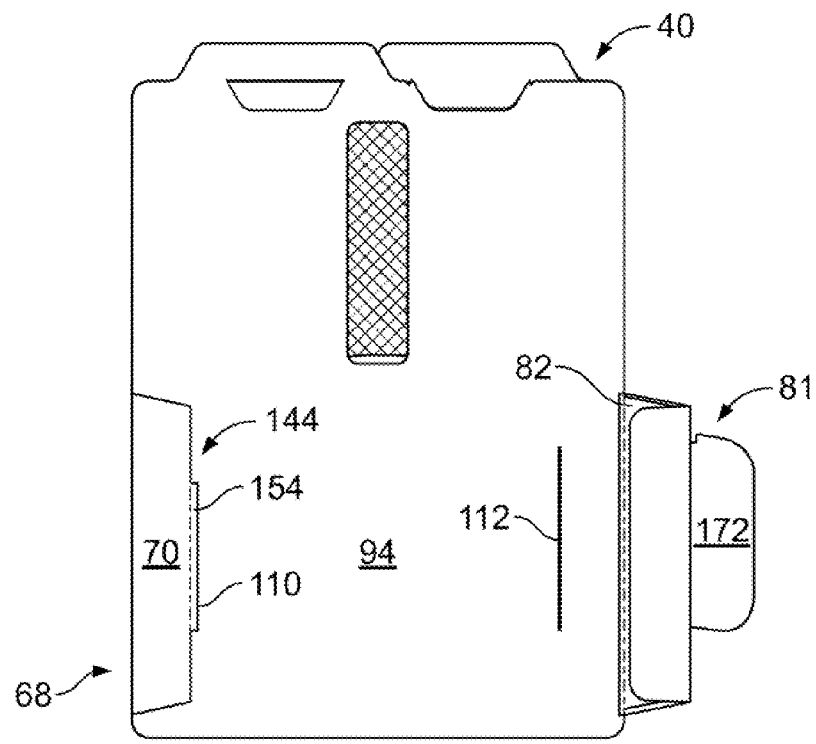
Figure 4F:
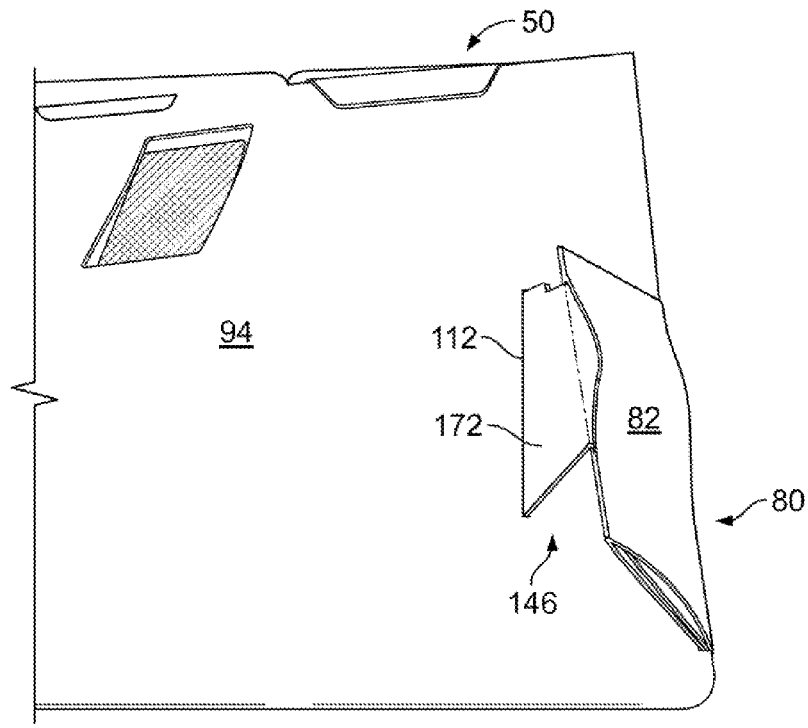
Figures 1, 4F:
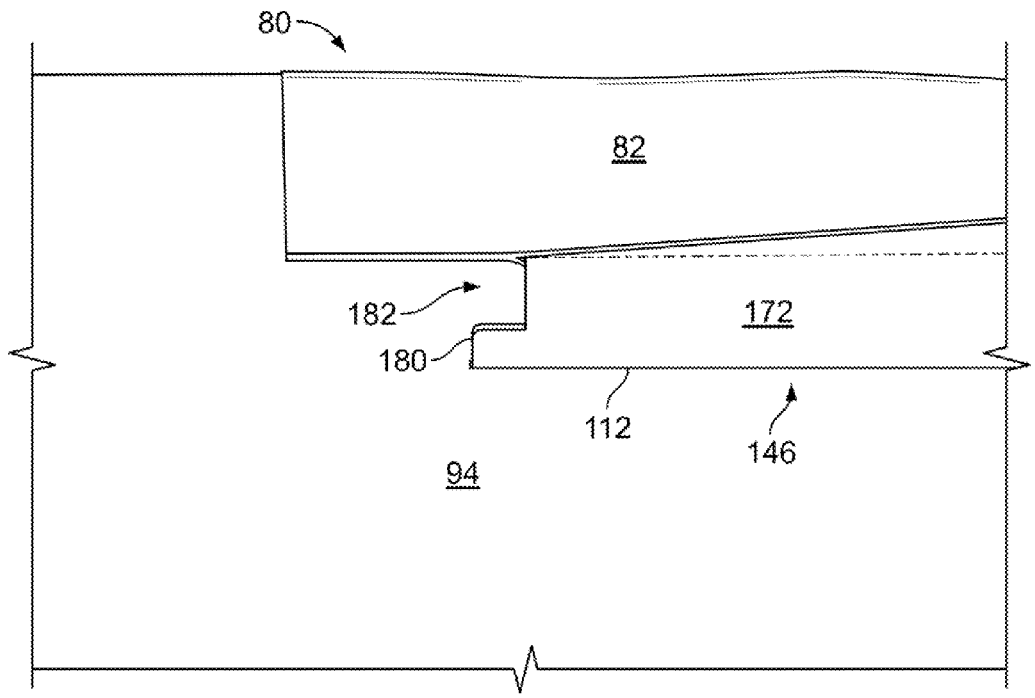

Referring to FIG. 4E, in one embodiment, the first foldable part 70 of the first foldable tab 68 may be folded over the top of the second panel 94 and the second foldable part 154 of the first lateral locking tab 144 may be inserted into the first locking slot 110 for closing a first side of the package 40. Referring to FIGS. 4E and 4F, in one embodiment, the first foldable part 82 of the second foldable tab 80 may be folded over the second panel 94 so that the second foldable part 172 of the second lateral locking tab 146 may be inserted into the second locking slot 112 of the second panel 94 of the outer component 50.

FIG. 4F-1 shows the second foldable part 172 of the second lateral locking tab 146 being inserted into the second locking slot 112 of the second panel 94 of the outer component. The first foldable part 82 of the second foldable tab 80 preferably overlies the second panel 94 of the outer component. The upper end 180 of the second foldable part 176 of the second lateral locking tab 146 desirably includes a locking recess 182 formed therein for reliably securing the second lateral locking tab 146 with the second panel 94 of the outer component 50.

Figure 4G:
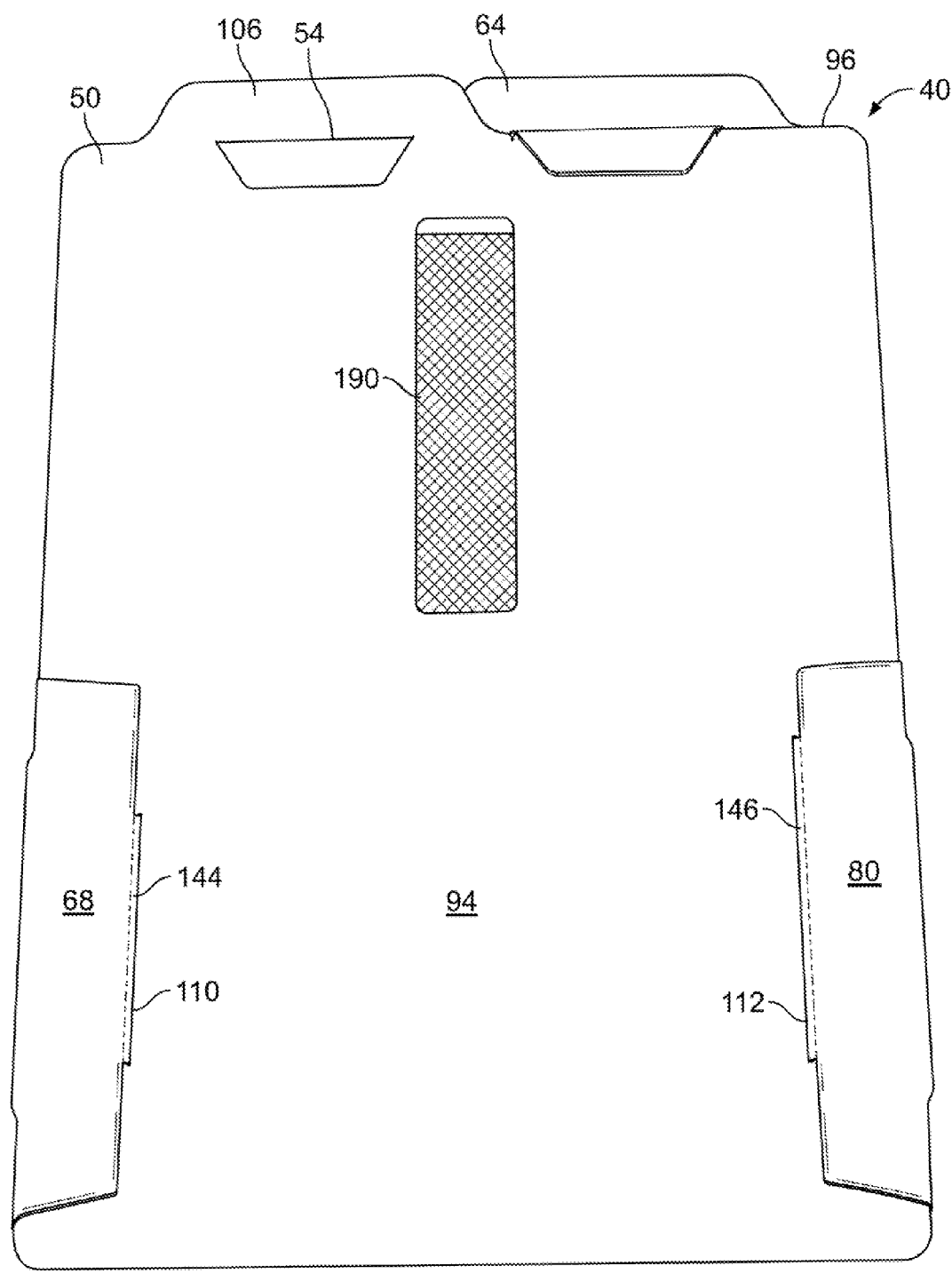

Referring to FIG. 4G, in one embodiment, after the first lateral locking tab 144 is inserted into the first locking slot 110 and the second lateral locking tab 146 is inserted into the second locking slot 112, the respective first and second foldable tabs 68, 80 desirably cover the sides of the first and second panels 52, 94 of the outer component 50 for holding the sides of the panels closed. The upper locking tabs 64, 106 preferably hold the upper edges 54, 96 of the respective first and second panels together for holding closed the upper ends of the panels of the package 40. The medical implant 190 may be held by the inner component 120 (FIG. 2a) and be disposed between the first and second panels 52, 94 of the outer component 50.

Figure 5A:
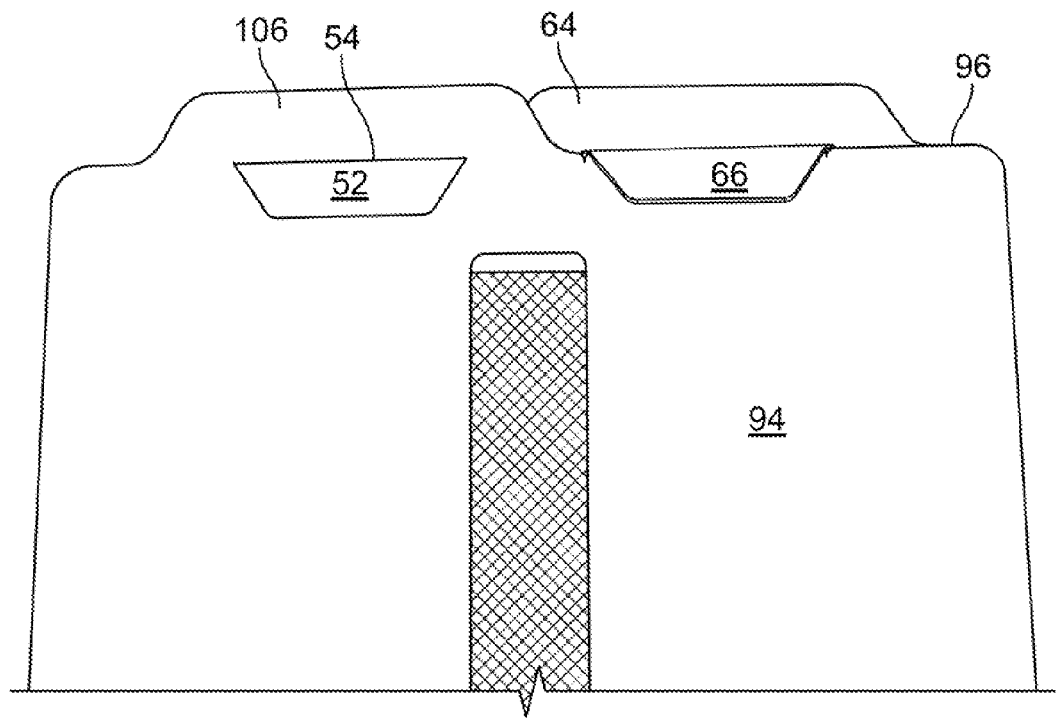
FIGS. 5A-5D show a method of unlocking an upper end of a package for dispensing a medical device, in accordance with one embodiment of the present invention.

Referring to FIG. 5A, in one embodiment, the second upper locking tab 106 preferably engages the upper edge 54 of the first panel 52 for closing the upper end of the package. Although not shown in FIG. 5A, the locking flap 108 of the second locking tab 106 desirably overlaps the upper edge 54 of the first panel 52. The locking flap 66 of the first upper locking tab 64 preferably overlies the upper edge 96 of the second panel 94 for holding the respective upper edges 54, 96 of the first and second panels 52, 94 together for closing the upper end of the package.

Figure 5B:
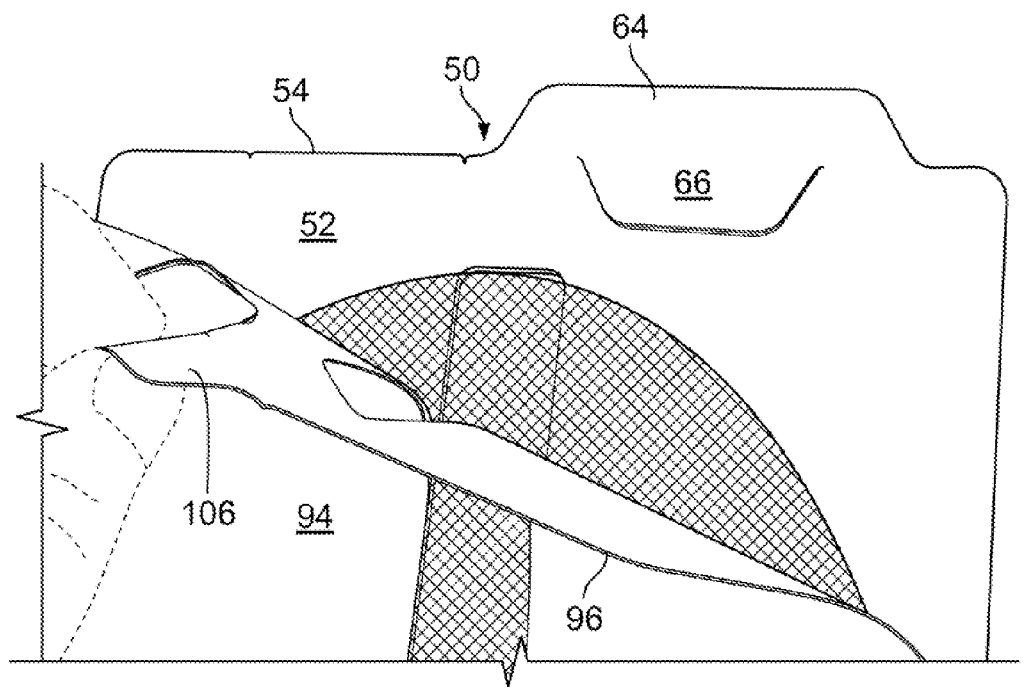

Referring to FIGS. 5A and 5B, in one embodiment, in order to open the upper end of the package, the second locking tab 106 is preferably pulled away from the upper edge 54 of the first panel 52 of the outer component 50. As the second locking tab 106 is pulled away from the first panel 52, the upper edge 96 of the second panel 94 is desirably released from the first locking flap 66 of the first upper locking tab 64.

Figure 5C:
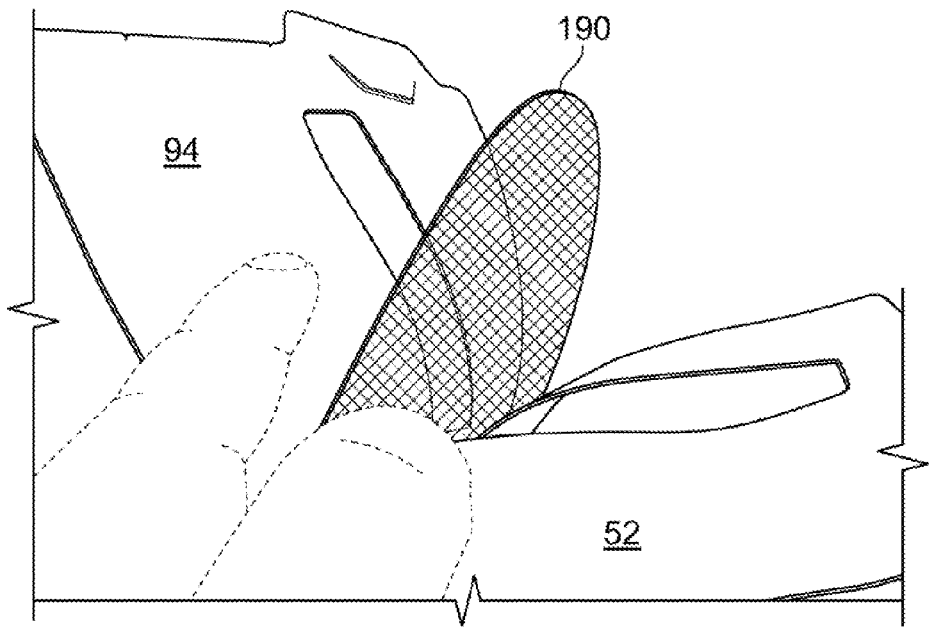
Figure 5D:
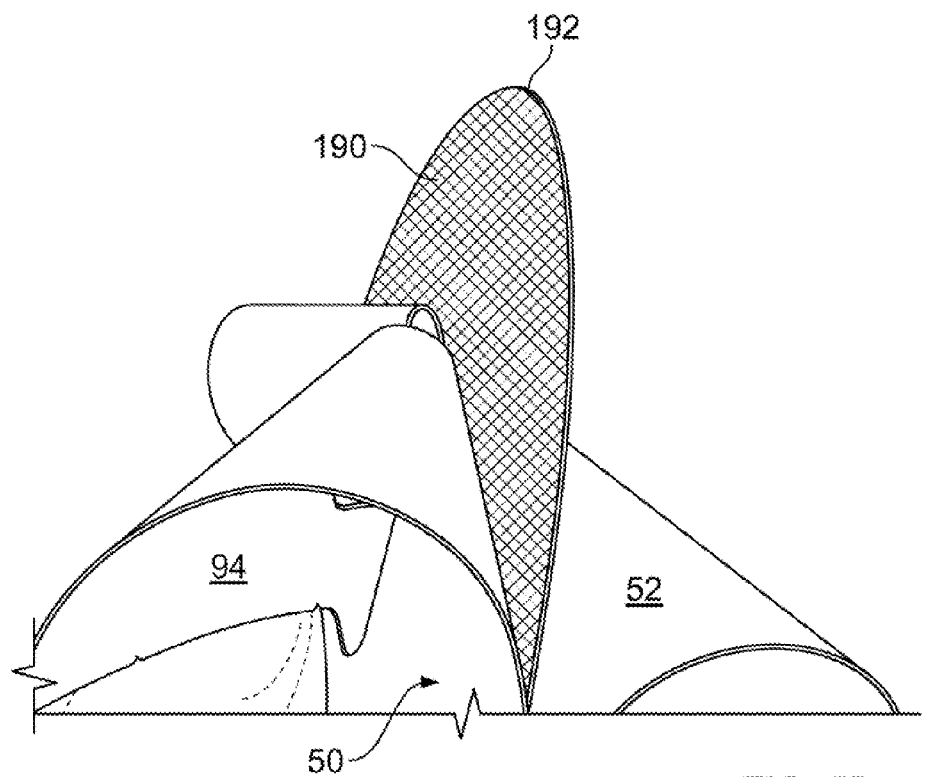

Referring to FIGS. 5B and 5C, in one embodiment, as the first and second panels 52, 94 are peeled or flexed away from one another, the medical implant 190 is desirably exposed and accessible at the upper end of the package. FIG. 5D shows how the medical implant 190 may project from the upper end of the medical package when the first and second panels 52, 94 are peeled away from one another. In FIG. 5D, the peripheral edge 192 of the medical implant 190 is accessible so that the implant may be removed from the package for use in a surgical procedure.

The packages for medical devices shown and described herein may be utilized to hold medical implants having various shapes and sizes. Although the medical implant 190 shown in FIGS. 1-5D has an oval shape, implants having other shapes and sizes may be contained within the packages disclosed herein, such as circular implants, square implants, and rectangular implants. The flat implants stored in a package may have a length of about 10-60 cm and a width of about 5-30 cm. Preferred implants may include those disclosed in commonly assigned U.S. patent application Ser. No. 12/815,275, the disclosure of which is hereby incorporated by reference herein.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A package for a medical device comprising:
   an outer component including a first panel and a second panel foldable over said first panel for closing said package;
   an inner component mechanically interlocked with said outer component, said inner component being stiffer than said outer component, wherein said inner component is adapted to be disposed inside said outer component when said package is closed, wherein said package is adapted to be opened while said outer and inner components remain mechanically interlocked together, and wherein when said second panel of said outer component is folded over said first panel of said outer component, said inner component has a first lateral locking tab insertable into a first locking slit on said second panel for mechanically interlocking said outer and inner components and for closing a first side of said package, and said inner component has a second lateral locking tab insertable into a second locking slit on said second panel for mechanically interlocking said outer and inner components and closing a second side of said package.

2. The package as claimed in claim 1, wherein said inner component is more hydrophilic than said outer component.

3. The package as claimed in claim 1, wherein said outer component comprises a hydrophobic material.

4. The package as claimed in claim 3, wherein said outer component comprises a synthetic material and said inner component comprises paper or paperboard.

5. The package as claimed in claim 1, wherein
said first locking slit extends along an axis that is parallel to a first lateral edge of said second panel and said second locking slit extends along an axis that is parallel to a second lateral edge of said second panel.

6. The package as claimed in claim 5, wherein said outer component further comprises:
a first foldable tab projecting from said first lateral edge of said first panel;
a second foldable tab projecting from said second lateral edge of said first panel, wherein said first and second locking slits on said second panel are aligned with said first and second foldable tabs on said first panel when said second panel is folded over said first panel.

7. The package as claimed in claim 6, wherein said inner component comprises:
said first lateral locking tab projecting from a first lateral edge of said inner component being adapted to mechanically interlock with said first foldable tab of said outer component; and
said second lateral locking tab projecting from a second lateral edge of said inner component being adapted to mechanically interlock with said second foldable tab of said outer component.

8. The package as claimed in claim 7, wherein said first foldable tab includes a slit extending parallel to said first lateral edge of said first panel that is adapted to receive said first lateral locking tab and said second foldable tab includes a slit extending parallel to said second lateral edge of said first panel that is adapted to receive said second lateral locking tab.

9. The package as claimed in claim 8, wherein each of said first and second lateral locking tabs includes a rounded lower end and an upper end including a locking recess and a gap toothed tab adjacent said locking recess.

10. The package as claimed in claim 9, wherein said locking recess on each of said first and second lateral locking tabs is oriented toward an upper, open end of said package.

11. The package as claimed in claim 9, wherein each of said first and second lateral locking tabs define a first length extending from said rounded lower end to said gap toothed tab thereof and each of said slits on said first and second foldable tabs define a second length, and wherein said first length is greater than said second length.

12. The package as claimed in claim 8, further comprising:
said first panel of said outer component having a lower end and an upper end with a first upper end locking tab;
said second panel of said outer component having a lower end and an upper end with a second upper end locking tab, said lower ends of said first and second panels being connected together along a score line that enables said second panel to be folded over said first panel whereupon said upper ends of said first and second panels are in substantial alignment with one another, wherein when said second panel is folded over said first panel said first upper end locking tab of said first panel is engageable with said upper end of said second panel and said second upper end locking tab of said second panel is engageable with said upper end of said first panel for closing an upper end of said package.

13. The package as claimed in claim 12, wherein said first upper end locking tab includes a first flexible flap adapted to engage said upper end of said second panel and said second upper end locking tab includes a second flexible flap adapted to engage said upper end of said first panel for holding said upper end of said package closed.

14. The package as claimed in claim 8, wherein said first lateral locking tab has a first side with a rounded surface for facilitating insertion of said first lateral locking tab into said first locking slit on said second panel and a second side with a locking recess adapted to retain said first lateral locking tab in said first locking slit on said second panel after being inserted into said first locking slit, and wherein said second lateral locking tab has a first side with a rounded surface for facilitating insertion of said second lateral locking tab into said second locking slit on said second panel and a second side with a locking recess adapted to retain said second lateral locking tab in said second locking slit on said second panel after being inserted into said second locking slit.

15. The package as claimed in claim 1, wherein said inner component includes a main panel having an upper end and a lower end and at least one set of opposing securing elements adapted to releasably secure a medical device to said inner component, wherein said opposing securing elements are oriented toward said upper end of said main panel for urging release of said medical device from said upper end of said main panel.

16. The package as claimed in claim 15, wherein said inner component further comprises a flexible cover hingedly secured to said lower end of said main panel that is adapted to fold over said main panel for at least partially covering a major face of said main panel of said inner component.

17. The package as claimed in claim 5, wherein at least one of said first and second panels of said outer component includes at least one window spaced inside the edges of said panels for providing visual access inside said package when said package is closed.

18. A package for a flat medical implant comprising:
a flexible outer component including a first panel and a second panel foldable over said first panel for closing said package;
an inner component mechanically interlocked with said flexible outer component, said inner component being more hydrophilic than said flexible outer component;
wherein with said second panel folded over said first panel, said inner component has a first lateral locking tab insertable into a first locking slit on said second panel for mechanically interlocking said outer and inner panels and closing a first side of said package and said inner component has a second lateral locking tab insertable into a second locking slit on said second panel for mechanically interlocking said outer and inner components and closing a second side of said package;

a flat medical implant held by said inner component, wherein upper ends of said first and second panels are peelable away from one another while said outer and inner components remains mechanically interconnected together for opening said package and accessing said flat medical implant at an upper end of said package.

19. The package as claimed in claim 18, wherein said inner component is stiffer than said flexible outer component.

20. The package as claimed in claim 19, wherein said flexible outer component comprises synthetic material and said inner component comprises cellulose material adapted to remove moisture from said flat medical implant.

21. The package as claimed in claim 20, wherein said flat medical implant comprises a laminate including a surgical mesh and at least one absorbable layer overlying said surgical mesh, wherein said inner component is adapted to remove moisture present in said medical implant and inside said package.

22. The package as claimed in claim 21, wherein the weight ratio of said inner component to said at least one absorbable layer of said flat medical implant is between about 3.9:1-5.5:1.

23. The package as claimed in claim 18, wherein said flat medical implant has a length of about 5-60 cm and a width of about 10-30 cm.

24. A package for a medical device comprising:

an outer component including a first panel and a second panel foldable over said first panel for closing said package; and an inner component mechanically interlocked with said outer component, wherein said inner component is adapted to be disposed inside said outer component when said package is closed, and wherein said package is adapted to be opened while said outer and inner components remain mechanically interlocked together;

wherein said inner component includes a main panel having an upper end and a lower and at least one set of opposing securing tabs adapted to releasably secure a medical device to said inner component, wherein said opposing securing tabs are oriented toward said upper end of said main panel for urging release of said medical device from said upper end of said main panel, and wherein said inner component has a first lateral locking tab projecting from a first lateral edge of said main panel that is insertable into a first locking slit on said second panel of said outer component for mechanically interlocking said outer and inner components and closing a first side of said package and a second lateral locking tab proiecting from a second lateral edge of said main panel that is insertable into a second locking slit on said second panel of said outer component for mechanically interlocking said outer and inner components and closing a second side of said package.

* * * * *